(12) United States Patent
Day et al.

(10) Patent No.: US 11,213,599 B1
(45) Date of Patent: Jan. 4, 2022

(54) FAR-UVC JEWELRY FOR ANTI-VIRUS PROTECTION

(71) Applicants: Michele Marie Day, Youngsville, LA (US); Alan Cook Day, Youngsville, LA (US)

(72) Inventors: Michele Marie Day, Youngsville, LA (US); Alan Cook Day, Youngsville, LA (US)

(73) Assignees: Michele Marie Day, Youngsville, LA (US); Alan Cook Day, Youngsville, LA (US)

(*) Notice: Subject to any disclaimer, the term of this patent is extended or adjusted under 35 U.S.C. 154(b) by 0 days.

(21) Appl. No.: 17/388,574

(22) Filed: Jul. 29, 2021

(51) Int. Cl.
| A44C 5/00 | (2006.01) |
| A44C 15/00 | (2006.01) |
| A61L 2/00 | (2006.01) |

(52) U.S. Cl.
CPC .......... *A61L 2/0047* (2013.01); *A44C 5/0023* (2013.01); *A44C 15/005* (2013.01); *A61L 2202/11* (2013.01)

(58) Field of Classification Search
CPC . A44C 5/0007; A44C 5/0023; A44C 15/0015; A44C 15/005; A41D 27/085; F21V 33/0004
See application file for complete search history.

(56) References Cited

U.S. PATENT DOCUMENTS

| 2021/0290791 A1* | 9/2021 | Mandaric | A61L 2/10 |
| 2021/0299298 A1* | 9/2021 | Root | A61L 2/26 |

OTHER PUBLICATIONS

Far-UVC light (22NM) efficiently and safely inactivates airborne human corona viruses. Bt Manuela Buonanno, David Welch, Igor Shuryak, David J. Brenner. Jun. 24, 2020. Scientific Reports 10, Article No. 10285 (2020). (Year: 2020).*

* cited by examiner

*Primary Examiner* — Jack W Lavinder
(74) *Attorney, Agent, or Firm* — Michele Marie Day; Alan Cook Day

(57) ABSTRACT

Far-Ultra-Violet C (Far-UVC) jewelry article with components thereof and other accessories is provided to protect wearer from intrusion of viruses and micro-organisms. The jewelry article is integrated with Far-UVC photons that project wavelengths of about 222 nanometers to protect against viruses. The jewelry article would be a type of necklace, bracelet, or ankle bracelet comprised of Far-UVC diodes attached on the jewelry projecting sterilizing rays on surfaces at a safe distance protecting skin and eyes.

3 Claims, 3 Drawing Sheets

Jewelry Necklace with Far-UVC Diodes

Jewelry Bracelet with Far-UVC Diodes

Jewelry Ankle Bracelet with Far-UVC Diodes

FAR-UVC JEWELRY FOR ANTI-VIRUS PROTECTION

BACKGROUND

With the pandemic of COVID19 and other types of viruses, sterilization while traveling or in crowded venues is key in maintaining health. Far-UVC light can be used for disinfecting, sterilizing, and destroying harmful micro-organisms on surfaces and in the air. In addition, parasitic insects have preyed on humans and animals causing diseases and even death. Application of Far-UVC lights article on jewelry, may be beneficial to eliminating viruses and insects before infecting humans.

Far-UVC lights are used to sterilize surfaces and when combined with wearable jewelry may prove beneficial in reducing the spread of viruses within crowds at hospitals, emergency rooms, construction sights, athletic stadiums, festivals carnivals, schools, colleges, churches, work environments, airports, malls, cities, or any venue with crowds of people. Far-UVC lights could be used in camping environments, farming, and any outdoor activity for humans and animals to remain safe from parasitic insects.

Far-UVC combined with wearable jewelry could potentially kill viruses living on money, cellphones or other objects used for handling or viruses near the person. Scientific studies have shown that viruses can live on some surfaces for up to 28 days and on skin for 11 days.

Far-UVC lights are currently found within wand applications, air filtration, and indoor lighting but have yet to be combined with wearable jewelry.

Therefore, a need exists for novel application of positioning Far-UVC lights within wearable jewelry to eliminate viruses or other micro-organisms before infecting a human.

REFERENCES CITED

With regard to the reference of the patent, Connor et al. (U.S. Ser. No. 13/967,987), differences remain in the distinction of the Far-UVC jewelry invention where the illumination of a shorter wavelength disseminates off the jewelry verses the Connor invention is a wearable device and method for disrupting unwelcome photography by a proximal imaging device in order to protect a person's privacy. The Far-UVC article with integration in jewelry allows for this invention with integration of Far-UVC photons to emit externally from the jewelry into the air or surfaces at 222 nanometers to kill viruses. This wavelength allows for the scientifically studied safety of Far-UVC rays near skin and eyes. The light mentioned in the Connor is an ambient light source to disrupt unwelcome photography; and an outbound light guide that directs light from the wearable light source, from the ambient light source, or from both the wearable light source and the ambient light source toward the proximal imaging device in order to disrupt unwelcome photography. The difference remains that this invention designed with Far-UVC is illuminated externally from jewelry versus an ambient light source specified by Connor's design. Far-UVC at a low level maintains scientifically safe standards to be on or near the skin and eyes while killing viruses in the air. In conclusion, the Wearable Far-UVC invention differs from the Connor patent referenced.

With regard to the reference of the patent, Finn (U.S. Pub. No. 2019/0014872A1), differences remain in the distinction of the Far-UVC jewelry invention where the illumination of approximately 222 nanometer wavelength article disseminates off the jewelry for protection against viruses verses the Finn patent consisting of a LED light attached to jewelry as a fashion statement.

With regard to the reference of the patent, Rife, (U.S. Pat. No. 9,078,495B2), differences remain in the distinction of the Wearable Far-UVC invention where the illumination of approximately 222 nanometer wavelength article disseminates off the jewelry verses the patent by Rife whereas the apparatus is ornamental on the jewelry to adjust the colors and illumination of the jewelry.

With regard to the reference of the patent, Slowinski (U.S. Pub. No. 2009/0235689A1), differences remain in the distinction of the Far-UVC jewelry invention where the illumination of approximately 222 nanometer wavelength article disseminates off the jewelry verses the patent by Slowinski which is a method and setting element to enhance a gemstone. The Slowinski patent design is for jewelry enhancement and ornamentation verses the Far-UVC jewelry designed for anti-virus protection.

With regard to the reference of the patent, D'Souza (U.S. Pat. No. 11,016,464), differences remain in the distinction of the Wearable Far-UVC jewelry invention where the illumination of approximately 222 nanometer wavelength article disseminates off the jewelry verses the patent by D'Souza where the LED lamination on jewelry is ornamental to produce a colored light effect and is an ornamental use to the wearer versus the Far-UVC jewelry invention to worn to protect from viruses.

BRIEF SUMMARY OF THE INVENTION

The present invention comprises a novel Far-UVC diode with jewelry. A novel design of the Far-UVC anti-virus diodes on jewelry emitting a wavelength of approximate 222 nanometers will allow the light to be activated when needed in crowds. The Far-UVC diode is illuminated on the structure of the jewelry to prevent, micro-organisms from landing on the skin with its sterilization properties. Fabric, leather, stone, plastics, latex, stone, rubber, foam, wood, metal alloys, aluminum, and other materials may comprise some or all of the elements of the positioning devices and apparatuses in various embodiments of the present invention. Far-UVC diodes positioned on the outside of jewelry could prevent the virus from infecting humans and could potentially clean viruses off surfaces. Far-UVC diodes will be affixed in a position on the jewelry to sterilize and prevent viruses from infection. Far-UVC at approximately 222 nanometers for wearable jewelry is safe to human cells due to the lower wavelength.

BRIEF DESCRIPTION OF THE DRAWING

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a", "an" and "the" are intended to use the plural forms as well as the singular forms, unless the context clearly indicates otherwise. It will be further understood that the terms "comprise" and/or "comprising" when used in this specification, specify the presence of stated features, steps, operations, elements, and/or components, but do not preclude the presence or addition of one or more of the features, steps, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formerly sense unless expressly so defined herein.

In describing the invention, it will be understood that a number of techniques and steps are disclosed. Each of these has individual benefit and each can be used in conjunction with one or more, or in some cases all, of the other disclosed techniques. Accordingly, for the sake of brevity, this description will refrain from repeating every possibly combination of the individual steps in an unnecessary fashion. Nevertheless, the specification and claims should be read with the understanding that such combinations are entirely within the scope of the invention and the claims.

Novel Wearable Far-UVC diodes are positioned on jewelry to repel micro-organisms from attaching to humans. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiment illustrated by the figures or description below.

Figure 1:
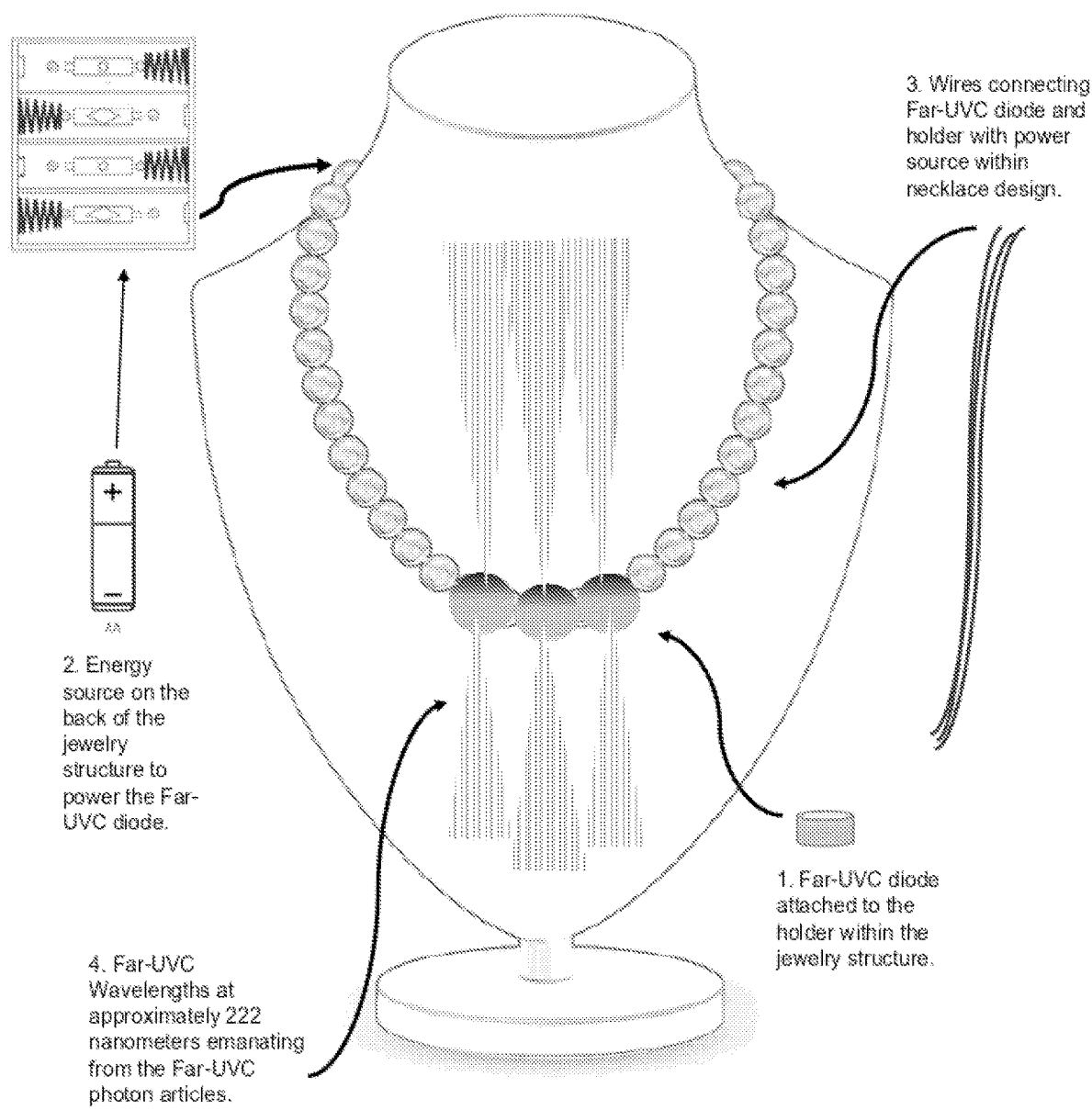
FIG. 1—FIG. 1 depicts an embodiment of a necklace with Far-UVC diode and holder affixed to the jewelry to potentially prevent the virus from attaching to the human skin as well as sterilizing surfaces touched with the Far-UVC wavelengths.

The present invention will now be described by referencing the appended figures representing preferred embodiments. FIG. 1 depicts the jewelry necklace view with the Far-UVC diode at about 222 nanometers, energy source, and wires affixed to the structure.

Figure 2:
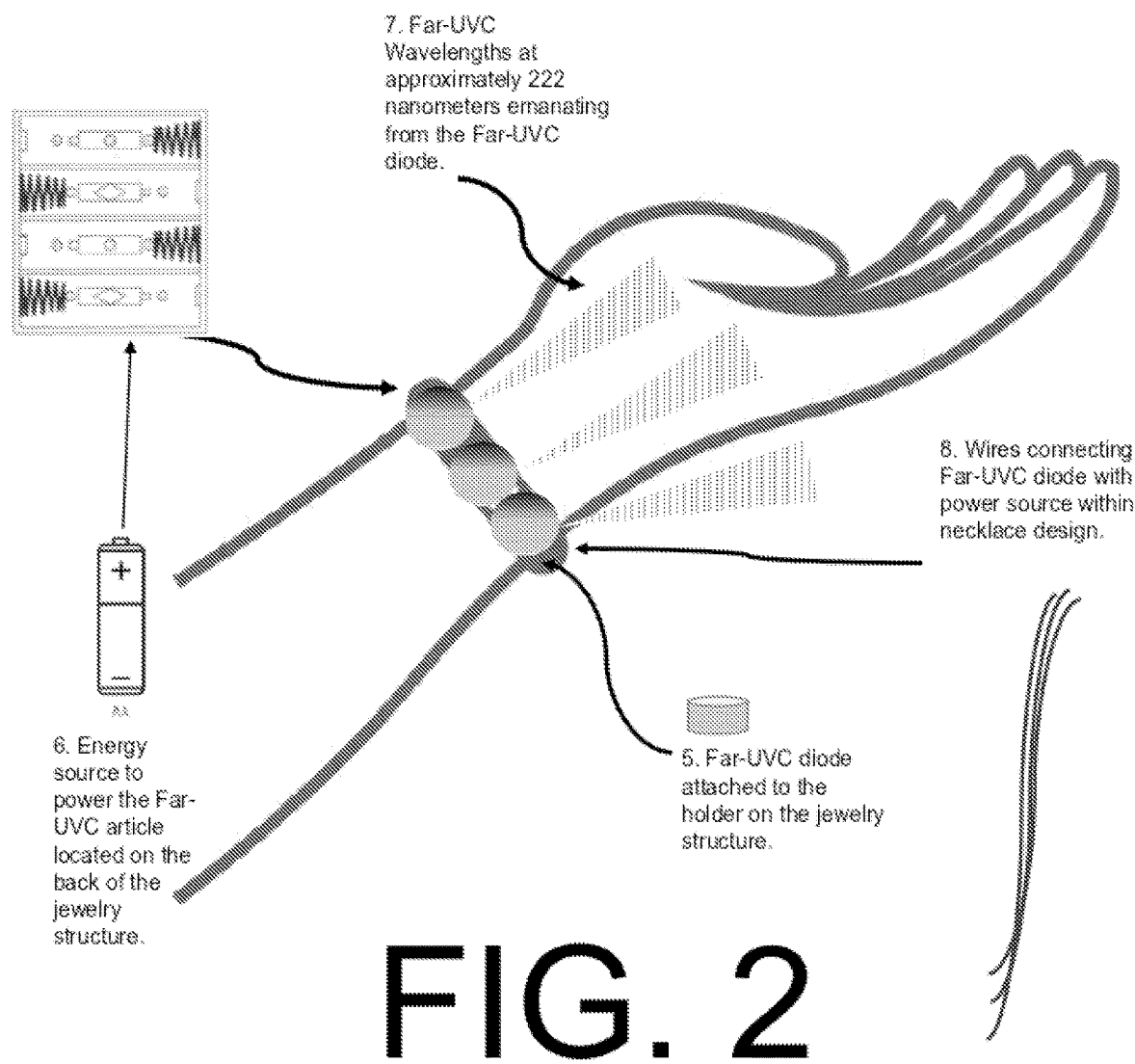
FIG. 2—FIG. 2 depicts a wrist bracelet perspective view of one example of the Far-UVC article placements according to the various embodiments of the present invention.

In FIG. 2 the elements of the invention represented depicts a jewelry bracelet view of the elements that may comprise a photon articles at about 222 nanometers, energy source, and wires affixed onto the wrist portion of the bracelet.

Figure 3:
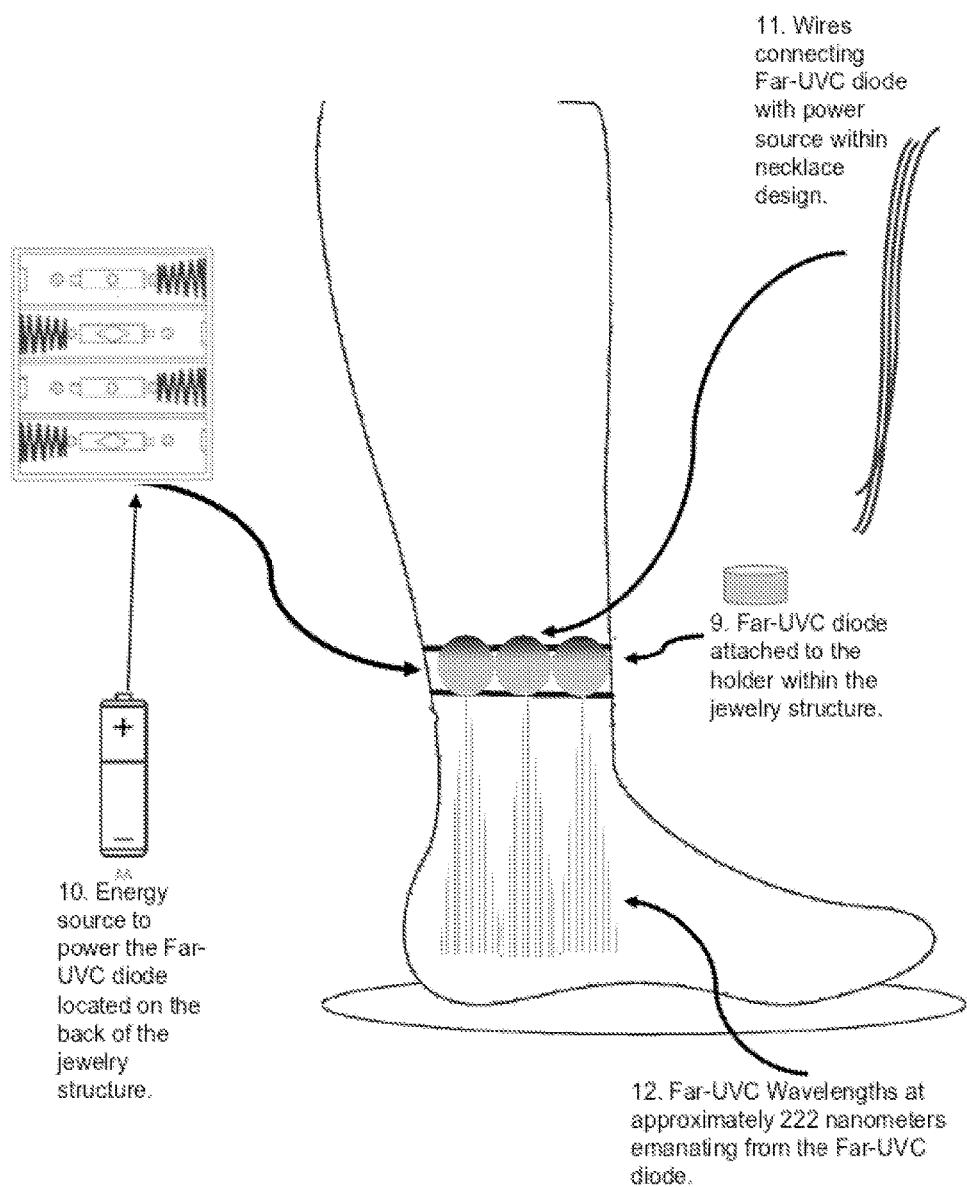
FIG. 3—FIG. 3 depicts an embodiment of an ankle bracelet with the Far-UVC wavelengths of approximately 222 nanometers emanating off the Far-UVC diode and holder affixed to the ankle bracelet structure.

In FIG. 3 the elements of the invention are represented as a jewelry ankle bracelet view with the Far-UVC wavelengths at approximately 222 nanometers emanating from the Far-UVC photon article along with the energy source, and wires.

While preferred materials for elements have been described, the device is not limited by these materials. Fabric, plastics, latex, stone, rubber, foam, wood, metal alloys, aluminum, and other materials may comprise some or all of the elements of the positioning devices and apparatuses in various embodiments of the present invention.

Although the present invention has been illustrated and described herein with reference to preferred embodiments and specific examples thereof, it will be readily apparent to those of ordinary skill in the art that other embodiments and examples perform similar functions and/or achieve like results. All such equivalent embodiments and examples are within the spirit and scope of the present invention, are contemplated thereby, and are intended to be covered by the aforementioned claims.

The invention claimed is:

1. A wearable Far-UVC jewelry article for anti-virus protection comprising:
   a jewelry article for fitting around a neck, a wrist, or an ankle with a substantially annular shaped outer edge with an exterior surface;
   a Far-UVC holder is positioned on said substantially annular shaped outer edge of the jewelry on the exterior surface;
   a plurality of Far-UVC diodes secured in said Far-UVC holder emitting a wavelength of light at approximately 222 nm substantially transverse to the annular shaped outer edge of the jewelry article.

2. A Far-UVC jewelry article of claim 1 further comprising a power source of one of a rechargeable battery, solar power, electromagnetism, or acoustic sound.

3. A Far-UVC jewelry article of claim 1 comprising the jewelry including one of a necklace, bracelet, or ankle bracelet.

* * * * *